(12) United States Patent
Senga et al.

(10) Patent No.: US 10,624,910 B2
(45) Date of Patent: Apr. 21, 2020

(54) THROMBIN-LIKE ENZYME FOR REDUCING A SIDE EFFECT OF AN ANTICANCER DRUG

(75) Inventors: Hirobumi Senga, Minato-ku (JP); Yongling Wan, Haidian District (CN)

(73) Assignee: TOBISHI PHARMACEUTICAL CO., LTD., Tokyo (JP)

( * ) Notice: Subject to any disclaimer, the term of this patent is extended or adjusted under 35 U.S.C. 154(b) by 695 days.

(21) Appl. No.: 12/743,162

(22) PCT Filed: Dec. 12, 2008

(86) PCT No.: PCT/JP2008/073133
§ 371 (c)(1),
(2), (4) Date: May 14, 2010

(87) PCT Pub. No.: WO2009/078474
PCT Pub. Date: Jun. 25, 2009

(65) Prior Publication Data
US 2010/0247510 A1    Sep. 30, 2010

(30) Foreign Application Priority Data
Dec. 14, 2007  (JP) ................. 2007-323600

(51) Int. Cl.
| | | |
|---|---|---|
| *A61K 31/675* | (2006.01) | |
| *A61K 38/48* | (2006.01) | |
| *A61K 31/704* | (2006.01) | |
| *A61K 45/06* | (2006.01) | |

(52) U.S. Cl.
CPC .......... *A61K 31/675* (2013.01); *A61K 31/704* (2013.01); *A61K 38/4833* (2013.01); *A61K 45/06* (2013.01)

(58) Field of Classification Search
CPC .............. A61K 31/675; A61K 38/4833; A61K 31/704; A61K 45/06
See application file for complete search history.

(56) References Cited

U.S. PATENT DOCUMENTS

| | | | |
|---|---|---|---|
| 4,137,127 A | 1/1979 | Stocker | |
| 2004/0180812 A1 | 9/2004 | Dicker et al. | |
| 2006/0088519 A1* | 4/2006 | Senga et al. | 424/94.64 |
| 2007/0104706 A1* | 5/2007 | Senga et al. | 424/94.64 |
| 2008/0253994 A1* | 10/2008 | Gulati et al. | 424/85.2 |

FOREIGN PATENT DOCUMENTS

| | | |
|---|---|---|
| JP | 57-010718 B2 | 2/1982 |
| JP | 3156112 B2 | 4/2001 |
| JP | 3482418 B2 | 12/2003 |

OTHER PUBLICATIONS

Day, "Treatment Sequencing, Asymmetry, and Uncertainty: Protocol Strategies for Combination Chemotherapy" (1986), Cancer Research, vol. 46: 3876-3885.*
Love et al. "Side Effects and Emotional Distress During Cancer Chemotherapy", Aug. 1988, Cancer: vol. 63: 604-612 (Year: 1989).*
Bonadona, "Phase I and Preliminary Phase II Evaluation of Adriamycin (NSC 123127)", Oct. 1970, Cancer Research: vol. 30: 2572-2582. (Year: 1970).*
Manjunatha, "Anticoagulant proteins from snake venoms: structure, function and mechanism", 2006, Bioch J., vol. 397: 377-387. (Year: 2006).*
International Search Report dated Feb. 24, 2009.
Written Opinion of the International Searching Authority dated Feb. 24, 2009.
J. Chmielewska et al., "Effect of Defibrination With Batroxobin on Growth and Metastasis of JW Sarcoma in Mice", Europ. J. Cancer, 1980, vol. 16, pp. 919-923.
J. William Lown et al., "Strand Scission of DNA by Bound Adriamycin and Daunorubicin in the Presence of Reducing Agents", Biochemical and Biophysical Research Communications, vol. 76, No. 3, 1977, pp. 705-710.
KF Stocker, "Medical Use of Snake Venom Proteins", ed., CRC Press, Boston, 1990, pp. 130-131.
KF Stocker, "Medical Use of Snake Venom Proteins", ed., CRC Press, Boston, 1990, pp. 134-135.
KF Stocker, "Medical Use of Snake Venom Proteins", ed., CRC Press, Boston, 1990, pp. 140-141.
Extended Search Report from European Patent Office issued in corresponding European Patent Application No. 08862566.0 dated Aug. 24, 2011.
Woodley-Cook, J. et al., "Effects of the Chemotherapeutic Agent Doxorubicin on the Protein C Anticoagulant Pathway," Molecular Cancer Therapeutics, Dec. 1, 2006, pp. 3303-3311, vol. 5, No. 12.
Damas, J. et al., "The Thrombopenic Effect of Ellagic Acid in the Rat. Another Model of Platelet Stimulation 'In Vivo'," Thrombosis Research, Jan. 15, 1987, pp. 153-163, vol. 45. No. 2, Tarrytown, NY.
Ramot, Y et al., "Drug-Induced Thrombosis—Experimental, Clinical, and Mechanistic Consideration," Society of Toxicologic Pathology, Feb. 1, 2007, pp. 208-225, vol. 35, No. 2, XP55004857, ISSN: 0192-6233.
Hilgard, P et al., "Anticoagulants in the Treatment of Cancer," European Journal of Cancer, Oct. 1, 1976, pp. 755-762, vol. 12, No. 10.
"Doxorubicin Ebewe Datasheet," Jan. 1, 2005, pp. 1-14, XP 55004947 http://www.medsafe.govt.nz/profs/datasheet/d/doxorubicinEbeweinj.pdf.
Japanese Office Action dated Jan. 10, 2013, issued in corresponding Japanese Patent Application No. 2010-523223.
M. Dimonpoulos et al., *Prospective randomized comparison of vincristine, doxorubicin and dexamethasone (VAD) administered as intravenous bolus injection and VAD with liposomal doxorubicin as first-line treatment in multiple myeloma*, 14 Journal of Oncology 1039-1044 (2003).

\* cited by examiner

*Primary Examiner* — Teresa E Knight
(74) *Attorney, Agent, or Firm* — Buchanan Ingersoll & Rooney PC

(57) ABSTRACT

The present invention provides an agent for reducing a side effect of an anticancer drug, which comprises a thrombin-like enzyme.

4 Claims, 2 Drawing Sheets

THROMBIN-LIKE ENZYME FOR REDUCING A SIDE EFFECT OF AN ANTICANCER DRUG

TECHNICAL FIELD

The present invention relates to an agent for reducing a side effect of an anticancer drug, which comprises a thrombin-like enzyme.

BACKGROUND ART

In recent years, with the early diagnosis and finding of cancer made possible through periodic medical examination, successful removal rate of the primary cancer by surgical operations has improved steadily. However, the multidrug chemotherapy or the combined therapy of chemotherapy and radiotherapy is still used for the treatment of late-stage cancer or the cancer accompanied by a metastatic focus.

Particularly, since the early diagnosis of malignant tumors with high-grade malignancy such as melanoma, lung cancer, liver cancer and pancreatic cancer is difficult, by the time the malignant tumor is diagnosed, the primary tumor, and metastatic tumor can already exist simultaneously, and surgical operations are impossible in many cases. In those cases, the combined chemotherapy with multi-anticancer drugs is widely used in treatment of such malignant tumors.

At present, cytotoxic anticancer drugs such as alkylating drugs, antimetabolites, anticancer antibiotics, plant alkaloids, platinum-based drugs are known for being the anticancer drugs widely used in clinic. However, cytotoxic anticancer drugs cause damage not only on cancer cells, but also on normal cells with active cytokinesis as well. Due to side effects caused by the cytotoxic anticancer drugs such as bone marrow suppression, cardiotoxicity, hematopoietic disorders, digestive disturbances, alopecia and the like, the effective quantity of the drug needed for cancer therapy cannot be administered, which is the fatal flaw of cytotoxic anticancer drugs.

Cyclophosphamide, an alkylating drug, is widely used in clinic, because of its effectiveness on acute leukemia, malignant lymphoma, multiple myeloma and the like. Cyclophosphamide is a drug that blocks cell proliferation by alkylating DNA, and thus suppressing DNA function. Since this drug blocks not only the proliferation of cancer cells but even the proliferation of normal cells, the side effects can occur. Vomiting, diarrhea, alopecia, bone marrow suppression and the like, are known to be the side effect.

Adriamycin (doxorubicin), an anticancer antibiotic, is widely used in clinic, and is effective in various kinds of cancers which include blood cancers such as acute leukemia and malignant lymphoma, and solid tumors such as lung cancer, breast cancer and osteosarcoma. However, it is known that adriamycin will cause side effects such as bone marrow suppression, cardiotoxicity, stomatitis, digestive disturbances and alopecia. In particular, the cardiotoxicity caused by adriamycin is a serious side effect which poses a clinical problem and causes the doses to be restricted. (William Lown J et al.: Strand scission of DNA by bound adriamycin and daunorubicin in the presence of reducing agents. Biochem. Biophys. Res. Commun., 76(3):705-710, 1977).

Cisplatin, a platinum-based drug, is a broad-spectrum anticancer drug. However, the clinical doses are to be restricted, because of the side effects such as digestive disturbances (mainly including nausea or vomiting), general malaise, kidney failure and hematopoietic disorders. Moreover, in order to reduce these side effects, a cisplatin derivative known as carboplatin was synthesized. Even though the side effects caused by carboplatin are lower than the side effects caused by cisplatin, the problem of carboplatin is the weak anticancer activity.

Under such conditions, the development of drug that reduces the side effects of anticancer drugs is strongly requested for clinical use. Until now, one agent was reported for reducing side effects of an anticancer drug. Such agent is characterized by comprising a nitrotriazole-derivative for reducing side effects of a cytotoxic anticancer drug (Japanese Patent No. 3482418). This reference has reported that a nitrotriazole-derivative suppresses the loss of body weight, which is the side effect of many anticancer drugs.

Moreover a pterin-derivative or neopterin derivative is reported as the active constituent of a cancer metastasis inhibitor and the side effect treating agent for anticancer drugs (Japanese Patent No. 3156112). This reference explains that the pterin and neopterin derivatives can suppress cancer metastasis, which leads to survival benefits; and reduces the side effects of anthraquinone anticancer drugs such as cardiotoxicity.

The thrombin-like enzyme, batroxobin which is derived from the venom of *Bothrops atrox moojeni*, was reported to be effective in the suppression of metastasis and proliferation of malignant tumors (Chmielewska J et al.: Effect of defibrination with batroxobin on growth and metastasis of JW sarcoma in mice. Europ. J. Cancer, 16:919-923, 1980). The technologies disclosed in this reference are based on the assumption that fibrinogen functions as a barrier to protect malignant tumor cells from the attacks of the immune system. In the technologies, a thrombin-like enzyme reduces fibrinogen levels, thus making it easier for the immune system to attack the malignant tumor cells, resulting batroxobin blocks the proliferation and metastasis of tumor cells. But, reported examples on the connection of batroxobin and reduction of the side effects of anticancer drugs do not exist.

DISCLOSURE OF INVENTION

The nitrotriazole derivative, the pterin derivative and the neopterin derivative in the patent documents described above are currently not used as drugs in clinic. Therefore, the development of a drug which can effectively reduce a side effect of an anticancer drug, in particular, severe side effect such as bone marrow suppression and cardiotoxicity, is strongly needed.

The inventors of the present application discovered, as a result of exhaustive research into the topics of the suppression of side effects such as bone marrow suppression and cardiotoxicity, which are caused by anticancer drugs such as cyclophosphamide, adriamycin and cisplatin, that batroxobin, a thrombin-like enzyme can reduce these side effects. The present invention is based on these findings.

Namely, the present invention relates to an agent for reducing a side effect of an anticancer drug, which comprises a thrombin-like enzyme. Specifically, the present invention is as follows:

(1) An agent for reducing a side effect of an anticancer drug, wherein the agent comprises a thrombin-like enzyme.
(2) The agent for reducing the side effect according to (1), wherein the thrombin-like enzyme is a protease which generates fibrin I from fibrinogen.
(3) The agent for reducing the side effect according to (1), wherein the thrombin-like enzyme is selected from the group consisting of batroxobin, ancrod and crotalase.

(4) The agent for reducing the side effect according to (1), wherein the thrombin-like enzyme is batroxobin.
(5) The agent for reducing the side effect according to (1), wherein the anticancer drug is a cytotoxic anticancer drug.
(6) The agent for reducing the side effect according to (5), wherein the cytotoxic anticancer drug is selected from the group consisting of an alkylating drug, an anticancer antibiotic and a platinum-based drug.
(7) The agent for reducing the side effect according to (5), wherein the cytotoxic anticancer drug is selected from the group consisting of cyclophosphamide, adriamycin and cisplatin.
(8) The agent for reducing the side effect according to (1), wherein the side effect is bone marrow suppression or cardiotoxicity caused by the anticancer drug.
(9) The agent for reducing the side effect according to (1), wherein the side effect is bone marrow suppression caused by the cytotoxic anticancer drug.
(10) The agent for reducing the side effect according to (9), wherein the cytotoxic anticancer drug is selected from the group consisting of an alkylating drug, an anticancer antibiotic and a platinum-based drug.
(11) The agent for reducing the side effect according to (9), wherein the cytotoxic anticancer drug is selected from the group consisting of cyclophosphamide, adriamycin and cisplatin.
(12) The agent for reducing the side effect according to (1), wherein the side effect is cardiotoxicity caused by the anticancer antibiotic.
(13) The agent for reducing the side effect according to (12), wherein the anticancer antibiotic is adriamycin.
(14) A method of reducing a side effect of an anticancer drug in a subject, comprising administering an effective amount of an thrombin-like enzyme to the subject.
(15) Use of a thrombin-like enzyme for the manufacture of an agent for reducing a side effect of an anticancer drug.

An agent for reducing a side effect of an anticancer drug of the present invention can effectively reduce a side effect of an anticancer drug; particularly the serious side effect such as bone marrow suppression and cardiotoxicity, as shown in the Examples below. Namely, by the administration of the present agent once or twice per day with simultaneous administration of the anticancer drug or after administration of the anticancer drug, the present agent can remarkably reduce the side effect of the anticancer drug. Therefore, the present invention can greatly contribute to the anticancer drug therapy.

BEST MODE FOR CARRYING OUT THE INVENTION

Figure 1:
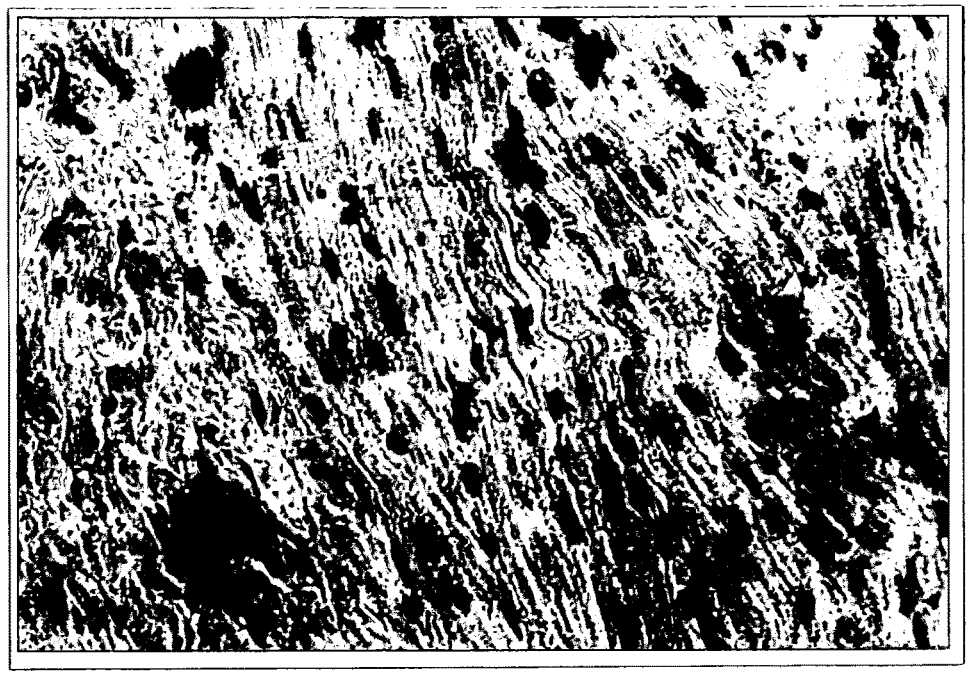
FIG. 1 is an optical microscopic photo (H&E stain, X400) of the left ventricular myocardial tissue of the control group.

The following provides a detailed explanation of this present invention.

It should be understood that the terms in the specification are used to have the meanings commonly used in the art, unless otherwise stated. Therefore, unless otherwise defined, all the technical terms and scientific terms, which are used in the specification, have the same meanings as what are generally understood by a person skilled in the art to which the present invention pertains. If the meaning of a term defined in the specification is different from that commonly used in the art, the meaning defined in the specification should be used in preference to that commonly used in the art.

The definitions of terms used in the present specification are enumerated below.

The term "a thrombin-like enzyme" used in the specification refers to a protease other than thrombin which has the characteristic of coagulating fibrinogen. Specific examples of the thrombin-like enzyme include batroxobin, ancrod, crotalase, flavoxobin, asperase, acutin, botropase, clotase, gabonase, venzyme and the like.

Thrombin-like enzymes are classified into 3 categories based on a site in the substrate, fibrinogen which the enzyme attacks: (i) a protease (such as batroxobin, ancrod and crotalase) that separates only fibrinopeptide A from fibrinogen to generate fibrin I; (ii) a protease (such as gabonase) that separates fibrinopeptide A and fibrinopeptide B from fibrinogen to generate fibrin II, which is also called fibrin; and (iii) a protease (such as venzyme) that mainly separates fibrinopeptide B from fibrinogen.

In the specification, the term "fibrin I" refers to a monomer generated when only fibrinopeptide A separates from fibrinogen. This fibrin I is also called Des A fibrin. Moreover, the term "fibrinopeptide A" is a peptide corresponding to the 16 amino acids at the $NH_2$ terminal end of the Act chain of fibrinogen.

Moreover, in the specification, batroxobin, ancrod, crotalase, flavoxobin, asperase, acutin and the like are mentioned as an example of the protease which generates fibrin I from fibrinogen.

The preferable thrombin-like enzyme of the present invention contains batroxobin, ancrod, crotalase (Stocker K F: Snake venom proteins affecting hemostasis and fibrinolysis, in *Medical Use of Snake Venom Proteins*, Stocker K F, ed., CRC Press, Boston, p130-131; 1990). Of these thrombin-like enzymes mentioned above, batroxobin is particularly preferable.

Batroxobin is a thrombin-like enzyme derived from the venom of *Bothrops atrox moojeni*, and a glycoprotein having the molecular weight of 36,000 Da.

Thrombin is an enzyme which has a glycoprotein structure, where prothrombin, which exists in the living body, is activated. In the basis of the glycoprotein structure, thrombin and batroxobin are similar enzymes. However, thrombin is different from batroxobin on the point where thrombin separates not only fibrinopeptide A but fibrinopeptide B from fibrinogen, and generates fibrin. Moreover, although batroxobin does not act on any blood coagulation factors other than fibrinogen, thrombin differs from batroxobin on the point that thrombin acts on blood coagulation factors other than fibrinogen.

Batroxobin is a known substance, and can be prepared according to the method described in Publication of examined Japanese patent application No. S57-10718 (Japanese Patent No. 1118129). Alternatively, it can be easily acquired from Tobishi Pharmaceuticals Co., Ltd. (Tokyo, Japan) and its subsidiary, Beijing Tobishi Pharmaceuticals, Co., Ltd. (Beijing, China).

Ancrod is a thrombin-like enzyme derived from the venom of *Agkistrodon rhodostoma*, and a glycoprotein having the molecular weight of about 35,400 Da. Ancrod is similar to batroxobin, in that they are both thrombin-like enzymes that separate only fibrinopeptide A from fibrinogen to generate fibrin I (Stocker K F: Snake venom proteins affecting hemostasis and fibrinolysis, in *Medical Use of Snake Venom Proteins*, Stocker K F, ed., CRC Press, Boston, p134-135; 1990).

Crotalase is a thrombin-like enzyme derived from the venom of the *Crotalus adamanteus*, and a glycoprotein having the molecular weight of about 32,700 Da. Crotalase is similar to batroxobin in that they are both thrombin-like enzymes which separate only fibrinopeptide A from fibrinogen to generate fibrin I (Stocker K F: Snake venom proteins affecting hemostasis and fibrinolysis, in *Medical Use of Snake Venom Proteins*, Stocker K F, ed., CRC Press, Boston, p140-141; 1990).

The thrombin-like enzymes above-mentioned such as batroxobin, ancrod and crotalase in the present invention can be a natural product or genetic recombinant product.

The term "an anticancer drug" in the present invention refers to a drug used in cancer therapy. Concrete examples of the anticancer drug include a cytotoxic anticancer drug, a molecular target-based drug, hormone and the like.

The term "a cytotoxic anticancer drug" refers to an anticancer drug which demonstrates any influence on the DNA of a nucleus or the cell cycle to exert the anticancer effect. Concrete examples of the cytotoxic anticancer drug include an alkylating agent, an antimetabolite, an anticancer antibiotic, a platinum-based drug and a plant alkaloid and the like.

The alklyating agent includes nitrogen mustard N-oxide hydrochloride, melphalan, cyclophosphamide, ifosfamide and other nitrogen mustard; carboquone, thiotepa and other ethyleneimines; nimustine hydrochloride, ranimustine and other nitrosoureas and the like.

The antimetabolite includes methotrexate and other folic acid antagonists; fluorouracil, tegafur, carmofur and other pyrimidine antagonists; cytarabine, cyclocytidine, enocitabine and other cytosine arabinoside; mercaptopurine, thioinosine and other purine antagonists and the like.

The anticancer antibiotic includes adriamycin, doxorubicin, daunorubicin, aclarubicin, pirarubicin and other anthracyclines; bleomycin, pepleomycin and other bleomycins; mitomycin C and other mitomycins actinomycin D and other actinomycins; neocarzinostatin and other polypeptides and the like.

The platinum-based drug includes cisplatin, carboplatin, nedaplatin, oxaliplatin and the like.

The plant alkaloid includes, vinblastine, vincristine, vindesine, paclitaxel, docetaxel, etoposide, camptothecine, irinotecan and the like.

The present agent can demonstrate being particularly effective in reducing a side effect of cyclophosphamide, adriamycin and cisplatin.

In addition, the present agent can demonstrate the action of reducing not only a side effect that occurs with administration of the anticancer drug alone, but also reducing a side effect that occurs with concurrent administration of multiple anticancer drugs.

The term "a side effect of an anticancer drug" refers to a therapeutically unnecessary effect seen at the time of the anticancer drug administration, or an effect which may cause clinical disturbance.

Examples of the side effect of the anticancer drug include bone marrow suppression, cardiotoxicity, hair loss, digestive disturbances (including nausea, vomiting, diarrhea), renal dysfunctions, general malaise, stomatitis and the like. Of these mentioned side effects, the present invention can demonstrate great ability in reducing the severe side effect such as bone marrow suppression and cardiotoxicity.

The term "bone marrow suppression" means the reduction of red blood cells (RBCs), white blood cells (WBCs), and platelets (Plts) that are caused when an anticancer drug damages the normal heamatopoietic cells. Symptoms that originate from bone marrow suppression include anemia due to hematopoietic injury, infections due to leukopenia, hemorrhages due to thrombocytopenia, and the like. The bone marrow suppression is the side effect that occurs easily when a cytotoxic anticancer drug (particularly an alkylating drug, anticancer antibiotic, and platinum-based drug) is used. When the degree of severity of bone marrow suppression is worst, hematopoietic stem cells that produce WBCs, RBCs and Plts, are destroyed. Some times such destruction causes serious anemia, fatally infectious diseases, hemorrhages (intracranial, gastrointestinal, pneumonorrhagia), and finally, it may be resulting death. Accordingly, bone marrow suppression is the side effect with high severity.

The term "cardiotoxicity" means the disturbance in myocardial tissues or myocardial cells which was caused by an anticancer drug. It is mentioned that symptoms such as congestive heart failure and arrhythmia and the like originate from cardiotoxicity. Cardiotoxicity is the side effect which happens easily when an anticancer antibiotic (especially anthracycline including adriamycin) is used. In histopathological studies, distinct contraction bands in myocardial tissue is an evaluation criteria of cardiotoxicity. The degree of cardiotoxicity is dependent on the dosage on the anticancer drug. When the degree of the severity of cardiotoxicy is high, it causes congestive heart failure, finally may be resulting death. Accordingly, the cardiotoxicity is the side effect with high severity.

The present invention can be greatly effective in reducing a side effect caused by cyclophosphamide, cisplatin and adriamycin. The typical side effect caused by cyclophosphamide, cisplatin and adriamycin is as follows:

Cyclophosphamide

Bone marrow suppression, vomiting, diarrhea, alopecia and the like

Adriamycin

Cardiotoxicity, bone marrow suppression, stomatitis, digestive disturbances, alopecia and the like Cisplatin Digestive disturbances, general malaise, bone marrow suppression, hematopoietic disorders, nephropathy and the like.

The term "reducing" means that a side effect, which is caused by an anticancer drug in the absence of the present agent, is alleviated by the administration of the present agent. The term "reducing" means that not only the side effect is alleviated by the present agent but also that the side effect itself does not occur by the present agent.

Any formulation in the Japanese Pharmacopeia General Rules for Preparations can be applied to the formulation of the present agent. Examples include injections for direct application inside the body (including suspensions and emulsions); ointments (including fatty ointments, emulsion ointments (creams), water-soluble ointments, and the like), inhalants, liquids (including ophthalmic solutions, collunarium, and the like), suppositories, patches, poutices, lotions and other external formulations; and internal formulations including tablets (including sugar-, film-, and gelatin-coated), liquids, capsules, granules, powders (including grains), pills, syrups, troches, and the like. These formulations can be prepared by the methods described in the Japanese Pharmacopoeia General Rules for Preparations.

Moreover, the present agent may also contain a pharmacologically acceptable solid or liquid carrier or an interventional therapy base, according to its dosage form. Examples of the pharmalogically acceptable solid or liquid carrier include a solvent, a stabilizer, a preservative, a solubilizing agent, an emulsifier, a suspending agent, a buffering agent, an isotonizing agent, a coloring agent, a thickener, an excipient, a lubricant, a binding agent, a disintegrating agent, a coating agent, a corrigent and the like.

Specific examples of the carrier include water, lactose, sucrose, fructose, glucose, mannitol, sorbitol and other sugars and sugar alcohols, crystalline cellulose, methylcellulose, ethylcellulose, hydroxypropylcellulose, low substituted hydroxypropylcellulose, hydroxypropylmethylcellulose, hydroxypropylmethylcellulose phthalate, hydroxypropylmethylcellulose acetate succinate, carmellose, carmellose calcium, carmellose sodium, croscarmellose sodium, carboxymethylethylcellulose, cellulose acetate phlthalate and other celluloses and related derivatives, corn starch, wheat starch, rice starch, potato starch, dextrin, pregelatinized starch, partly pregelatinized starch, hydroxypropyl starch, sodium carboxymethyl starch, cyclodextrin, pullulan and other starches and related derivatives, agar, sodium alginate, acacia, gelatin, collagen, shellac, tragacanth, xanthan gum (natural), and other natural polymers (seaweeds, plant mucilage, proteins and the like), polyvinylpyrrolidone, aminoalkyl methacrylate copolymer, methacrylic acid copolymer, carboxyvinyl polymer, polyvinyl alcohol, dimethylpolysiloxane and other synthetic polymers, olive oil, cacao butter, carnauba wax, beef tallow, hydrogenated oil, soybean oil, sesame oil, camellia oil, paraffin, liquid paraffin, yellow beeswax, white petrolatum, coconut oil, microcrystalline wax and other oils and fats, stearic acid, aluminum stearate, calcium stearate, magnesium stearate, triethyl citrate, triacetine, medium chain fatty acid triglyceride, hard fat, isopropyl myristate, and other fatty acids and derivatives thereof, glycerin, stearyl alcohol, cetanol, propylene glycol, macrogol and other alcohols and polyvalent alcohols, zinc oxide, dibasic calcium phosphate, precipitated calcium carbonate, synthetic aluminum silicate, silicon dioxide anhydride, kaolin, dried aluminum hydroxide gel, synthetic hydrotalcite, titanium oxide, talc, bentonite, magnesium aluminometasilicate, aluminum potassium sulfate, bismuth subgallate, bismuth subsalicylate, calcium lactate, sodium bicarbonate and other inorganic substances and metal salt compounds, sucrose esters of fatty acid, polyoxyl stearate, polyoxyethylene hydrogenated castor oil, polyoxyethylene polyoxypropylene glycol, sorbitan sesquioleate, sorbitan trioleate, sorbitan monostearate, sorbitan monopalmitate, sorbitan monolaurate, polysorbate, glyceryl monostearate, sodium lauryl sulfate, lauromacrogol and other surfactants, dyes, perfumes and the like.

Examples of the intervention therapy base include stents, artificial blood vessels, catheters, balloons and the like.

The present agent can be administered to a subject to which an anticancer drug is administered. Examples of the subject include mammals such as human, dog and cat. The present agent can be suitable for human use.

The administration time of the present agent can be determined according to the type, dosage of an anticancer drug. It is preferable to administer the present agent simultaneously with the anticancer drug or after administration of the anticancer drug.

The administered dose of the present agent varies depending on the patient's weight, disease's properties and conditions, but is for example 0.1-50 batroxobin Units (hereinafter referred to as BU) of batroxobin, as the thrombin-like enzyme, can be administered once per day, in the case of an adult human being. The preferred dose for an adult human being is one dose every other day (one dose is 1-20 BU). In the case of preparations for external use, the dose is 0.01-500 mg per gram.

A batroxobin unit is a unit indicating the enzymatic activity of batroxobin; with 2 BU being the activity to achieve coagulation in 19.0±10.2 seconds when 0.1 ml of batroxobin solution is added to 0.3 ml of standard human plasma containing citric acid at 37° C.

For example, the present agent can be administered to the subject by intravenous drip, intravenous injection, intraarterial injection, intramuscular injection, subcutaneous injection, intradermal injection, intracardiac injection, intraperitoneal injection, intrathecal injection, intrarectal administration, sublingual administration, nasal administration, percutaneous administration, inhalation or local administration into the injured organs and/or tissues of a formulation prepared by diluting a thrombin-like enzyme with physiological saline. Generally, it is preferable to dilute a thrombin-like enzyme with 100 ml or more of physiological saline and to administer the prepared formulation into a subject by drip infusion for 1 hour or more.

The thrombin-like enzyme, batroxobin is used in the present agent. The acute toxicity ($LD_{50}$ (BU/kg)) of batroxobin on mice, rats, rabbits and dogs is as follows in Table 1. The acute toxicity test was assessed by the intravenous administration of batroxobin.

TABLE 1

Acute Toxicity of Batroxobin (i.v.)

| Animal Species | $LD_{50}$ Value(BU/kg) |
|---|---|
| Mouse (ddy) | 192~210 |
| Rat (Wistar) | 105~110 |
| Rabbit (NW) | >300 |
| Dog (mongrel) | 190~208 |

Although the following provide a detailed explanation of the present invention by indicating Formulation and Examples thereof, the present invention is not limited to these Formulation and Examples.

Formulation 1

Using batroxobin as a thrombin-like enzyme, the agent for reducing a side effect of an anticancer drug which has the following composition, was manufactured.
Batroxobin (active ingredient) 10 BU
Chlorobutanol (preservative) 3 mg
Gelatin hydrolysate (stabilizer) 0.1 mg
Sodium chloride (isotonic agent) 9 mg
Hydrochloric acid (pH regulator) q.s.
Distilled water for injection up to 1 ml
Total volume 1 ml Example 1

The Reducing Effect of Batroxobin on Lethal Toxicity Caused by Adriamycin

The thrombin-like enzyme, batroxobin (hereinafter referred to as DF-521) was used, which is manufactured by Beijing Tobishi Pharmaceutical Co., Ltd. (Beijing, China) with a trade name of Dong Ling Di Fu.

The anticancer drug, adriamycin (hereinafter referred to as ADM) was used, which is manufactured by Hualian Pharmaceutical Factory of Shanghai Pharmaceutical (Group) Co., Ltd.

The laboratory animals, male C57BL/6 mice (weight: 19-22 g) were divided into three groups: control group, adriamycin group (ADM group), and adriamycin+batroxobin group (ADM+DF-521 group), with 10 mice in each group. The control group was administered with physiological saline.

The adriamycin group was given an intraperitoneal dose (3 mg/kg) of adriamycin once every other day. The adriamycin+batroxobin group was given a simultaneous dosage of 3 mg/kg of adriamycin and 30 BU/kg of batroxobin intraperitoneally, once every other day. The drug administration was performed in total of 18 times. The experiment was terminated on the 41th day after the first dose administered. The number of deaths was totaled, and the survival rate was calculated from mortality rate. The results are presented in Table 2.

TABLE 2

| Group | Survival No/Total No (survival rate %) |
|---|---|
| Control | 10/10 (100%) |
| ADM | 4/10* (40%) |
| ADM + DF-521 | 10/10# (100%) |

*p < 0.05 comparision with control group.
p < 0.05 comparision with ADM group

As shown in Table 2, six mice in the adriamycin group died. It is thought that the death of mice is due to general side effects such as bone marrow suppression, cardiotoxicity and the like caused by adriamycin. On the other hand, all mice in the adriamycin+batroxobin group survived. The result means the survival rate of the adriamycin+batroxobin group is significantly higher (p<0.05) than the survival rate of the adriamycin group. It shows that batroxobin can reduce the side effects caused by adriamycin.

Example 2

The Reducing Effect of Batroxobin on Bone Marrow Suppression Caused by Cyclophosphamide The thrombin-like enzyme, batroxobin (hereinafter referred to as DF-521) was used, which is manufactured by Beijing Tobishi Pharmaceutical Co., Ltd. (Beijing, China) with a trade name of Dong Ling Di Fu.

The anticancer chug, cyclophosphamide (hereinafter referred to as CPA) was used, which is manufactured by Shanxi Powerdone Pharmaceutical Co., Ltd.

The laboratory animals, male C57BL/6 mice (weight: 20-240 were divided into three groups: control group, cyclophosphamide group (CPA group), and cyclophosphamide+batroxobin group (CPA+DF-521 group), with five mice in one group. The control group was given physiological saline once every other day. The cyclophosphamide group was given an intraperitoneal dose of 100 mg/kg of cyclophosphamide once every other day. The cyclophosphamide+batroxobin group was given an intraperitoneal dose of 100 mg/kg of cyclophosphamide and 30 BU/kg of batroxobin simultaneously, once every other day. After the fourth administration (7 days after the first administration), blood was collected from the femoral artery under ether anesthesia using the EDTA anticoagulant, and the white blood cell count (WBC), red blood cell count (RBC), hemoglobin value (Hb), and platelet count (Plt) was measured.

The bone marrow nuclear cell count (BMNC) per femur of a mouse was measured by the following procedure. Bone marrow was sampled from 2 femora of a mouse, the marrow was flushed with 2 ml of physiological saline, and made the bone marrow cell suspension. Twenty μl of bone marrow cell suspension was put into 3800 of 3% acetic acid solution. After the red blood cells were destroyed, the hemocytometer was used for counting the BMNC count under the microscope. Then the BMNC count per femur was calculated.

The above-mentioned BMNC, WBC, RBC, Plt counts and Hb value are used as an evaluation index for bone marrow suppression caused by cyclophosphamide. The results are shown in Table 3.

TABLE 3

| Group | BMNC ($\times 10^6$/bone) | WBC ($\times 10^9$/L) | RBC ($\times 10^{12}$/L) | Hb (g/L) | Plt ($\times 10^9$/L) |
|---|---|---|---|---|---|
| Control | 13.5 ± 2.3 | 5.6 ± 1.8 | 8.0 ± 1.1 | 118.2 ± 22.0 | 1022.0 ± 147.7 |
| CPA | 2.4 ± 0.4** | 0.8 ± 0.3** | 6.2 ± 0.5* | 98.8 ± 9.2 | 1081.6 ± 47.4 |
| CPA + DF-521 | 3.3 ± 0.4**## | 1.3 ± 0.1**## | 6.2 ± 0.5* | 98.4 ± 5.4 | 973.0 ± 177.1 |

*p < 0.05 compared with the control group
**p < 0.01 compared with the control group
p < 0.01 compared with the CPA group The BMNC, WBC, RBC counts of the cyclophosphamide group were significantly decreased than the control group (p<0.05 or p<0.01). On the other hand, the BMNC and WBC counts of the cyclophosphamide+batroxobin group were significantly higher than the BMNC and WBC counts of the cyclophosphamide group (p<0.01). Also, when the RBC and Plt counts and Hb value of the cyclophosphamide+batroxobin group were compared with those of the cyclophosphamide group, no change was seen.

In the present Example, it was confirmed that batroxobin can reduce the decrease of BMNC count and WBC count caused by cyclophosphamide. Therefore, it is understood that batroxobin can reduce the bone marrow suppression caused by cyclophosphamide.

Example 3

The Reducing Effect of Batroxobin on Bone Marrow Suppression Caused by Adriamycin The thrombin-like enzyme, batroxobin (hereinafter referred to as DF-521) was used, which is manufactured by Beijing Tobishi Pharmaceutical Co., Ltd. (Beijing, China) with a trade name of Dong Ling Di Fu.

The anticancer drug, adriamycin (hereinafter referred to as ADM) was used, which is manufactured by Hualian Pharmaceutical Factory of Shanghai Pharmaceutical Group Co., Ltd.

The laboratory animals, C57BL/6 Mice (weight: 19-22 g) were divided into three groups: control group, adriamycin group (ADM group), and adriamycin+batroxobin (ADM+DF-521 group), with 5-10 mice (n=5 or 10) in one group. The control group was given physiological saline once every other day. The adriamycin group was given an intraperitoneal dose of 3 mg/kg of adriamycin once every other day. The adriamycin+batroxobin group was given an intraperitoneal doses of 3 mg/kg of adriamycin and 30 BU/kg of batroxobin simultaneously, once every other day. After the 9th administration, the experiment was terminated, and the blood was collected from the femoral artery under ether anesthesia using the EDTA anticoagulant. Then, the WBC, RBC counts and Hb value were measured.

Furthermore, the bone marrow nuclear cell (BMNC) count per femur of a mouse was measured with the following procedure. The bone marrow was sampled from 2 femora of a mouse, bone marrow was flushed with the 2 ml physiological saline, and made the bone marrow cell suspension. Twenty of marrow cell suspension was put into 380 μl of 3% acetic acid solution. After the red blood cells were destroyed, the hemocytometer was used for counting the BMNC count under the microscope. Then the BMNC count per femur was calculated.

The above-mentioned BMNC, RBC, WBC counts and Hb value were used as an evaluation index for bone marrow suppression caused by adriamycin. The results are shown in Table 4.

In the present Example, it was confirmed that batroxobin can reduce the decrease of BMNC count and Hb value caused by adriamycin. Therefore, it is understood that batroxobin can reduce bone marrow suppression caused by adriamycin.

Example 4

The Reducing Effect of Batroxobin on Bone Marrow Suppression Caused by Cisplatin The thrombin-like enzyme, batroxobin (hereinafter referred to as DF-521) was used, which is manufactured by Beijing Tobishi Pharmaceutical Co., Ltd. (Beijing, China) with a trade name of Dong Ling Di Fu.

The anticancer drug, cisplatin (hereinafter referred to as DDP) was used, which is manufactured by Yunnan Gejiu Biochemical Pharmaceutical Co., Ltd.

The laboratory animals, male C57BL/6 Mice (weight: 20-22 g) were divided into 3 groups: control group, cisplatin group (DDP group), and cisplatin+batroxobin group (DDP+DF-521 group); with 10 mice in one group. The control group was given physiological saline once every other day. The cisplatin group was given an intraperitoneal dose of 0.8 mg/kg of cisplatin once every other day. The cisplatin+batroxobin group was given an intraperitoneal dose of 0.8 mg/kg of cisplatin and 30 BU/kg of batroxobin simultaneously, once every other day. After the 17th administration (33rd day after the first administration), the experiment was terminated, blood was collected from the femoral artery under ether anesthesia using the anticoagulant EDTA, and the WBC, RBC, Plt counts and Hb value, were measured.

Furthermore the bone marrow nuclear cell (BMNC) count per femur of a mouse was measured by the following procedure. Bone marrow was sampled from 2 femora of a mouse, the bone marrow was flushed with the 2 ml physi-

TABLE 4

| Group | n | BMNC (×10$^6$/bone) | WBC (×10$^9$/L) | RBC (×10$^{12}$/L) | Hb (g/L) |
| --- | --- | --- | --- | --- | --- |
| Control | 5 | 11.4 ± 1.4 | 5.4 ± 0.7 | 9.6 ± 0.2 | 148.6 ± 2.2 |
| ADM | 10 | 6.9 ± 1.6** | 3.4 ± 0.7** | 6.6 ± 1.5** | 94.9 ± 30.5** |
| ADM + DF-521 | 10 | 8.6 ± 1.9**# | 3.5 ± 0.6** | 7.5 ± 0.5** | 116.5 ± 7.9**# |

**p < 0.01 compared with control group
p < 0.05 compared with the ADM group

In the adriamycin group, the BMNC, WBC, RBC counts and Hb value were all significantly decreased compared to the control group (p<0.01). On the other hand, the BMNC count and Hb value of the adriamycin+batroxobin group were significantly higher compared with the adriamycin group (p<0.05). Moreover, there was no change in the WBC count of the adriamycin+batroxobin group when compared with the adriamycin group. However, although the RBC count of the adriamycin+batroxobin group displayed an upward trend compared to the adriamycin group, there was no statistically significant difference between these two groups.

ological saline, and made bone marrow cell suspension. Twenty μl of marrow cell suspension was put into 380 μl of 3% acetic acid solution. After the red blood cells were destroyed, the hemocytometer was used for counting the BMNC count under the microscope. Then, the BMNC count per femur was calculated.

The above-mentioned BMNC, WBC, RBC, Plt counts and Hb value were used as an evaluation index for bone marrow suppression caused by cisplatin. The results are shown in Table 5.

TABLE 5

| Group | BMNC (×10⁶/bone) | WBC (×10⁹/L) | RBC (×10¹²/L) | Hb (g/L) | Plt (×10⁹/L) |
|---|---|---|---|---|---|
| Control | 16.8 ± 3.4 | 6.4 ± 1.7 | 7.6 ± 0.6 | 114.3 ± 10.6 | 1474.0 ± 193.0 |
| DDP | 11.3 ± 2.6** | 6.1 ± 2.2 | 7.4 ± 0.8 | 121.6 ± 10.7 | 1059.2 ± 241.5** |
| DDP + DF-521 | 14.7 ± 3.6# | 5.8 ± 1.3 | 8.2 ± 0.3*## | 134.0 ± 5.2**## | 1280.6 ± 167.4*# |

*$p < 0.05$ comparision with the control group
**$p < 0.01$ compared with the control group
$p < 0.05$ compared with the DDP group
$p < 0.01$ compared with the DDP group The BMNC and Plt counts of the cisplatin group were significantly decreased than those of the control group ($p<0.01$). But, the WBC, RBC counts and Hb value of the cisplatin group were not changed compared to the control group. On the other hand, the BMNC and Plt counts of the cisplatin+batroxobin group were significantly higher than the BMNC and Plt counts of the cisplatin group ($p<0.05$). Moreover, although RBC count and Hb value of the cisplatin+batroxobin group were significantly higher than those of the cisplatin group ($p<0.05$ and $p<0.01$), there was no difference in the WBC count between the cisplatin+batroxobin group and the cisplatin group.

In the present Example, it was confirmed that batroxobin can reduce the decrease of BMNC and Pit counts caused by cisplatin. Therefore, it is understood that batroxobin can reduce the bone marrow suppression caused by cisplatin.

Example 5

The Reducing Effect of Batroxobin on Cardiotoxicity Caused by Adriamycin

The thrombin-like enzyme, batroxobin (hereinafter referred to as DF-521) was used, which is manufactured by Beijing Tobishi Pharmaceutical Co., Ltd. (Beijing, China) with a trade name of Dong Ling Di Fu.

The anticancer drug, adriamycin (hereinafter referred to as ADM) was used, which is manufactured by Shenzhen Main Luck Pharmaceuticals Inc.

The laboratory animals, C57BL/6 male mice (weight: 16-18 g) were divided into 4 groups: 10 mice in the control group, 7 mice in the batroxobin group, 7 mice in the adriamycin group, and 7 mice in the adriamycin+batroxobin group. Mice from each group were inoculated with a dorsal right lateral subcutaneous injection of $3\times10^6$ B16-BL6 murine malignant melanoma cells in 0.3 ml of tumor cell suspension. After one day of tumor cell inoculation, the control group was given an intraperitoneal injuction of physiological saline once a day; the batroxobin group was given an intraperitoneal injection of batroxobin (20 BU/kg) once a day; the adriamycin group was given an intraperitoneal injection of adriamycin (3 mg/kg) once interval of 2 days; the adriamycin+batroxobin group was given an intraperitoneal injection of adriamycin (3 mg/kg) once interval of 2 days and an intraperitoneal injection of 20 BU/kg batroxobin once a day after administration of adriamycin. After 20 continuous days of administration, the hearts in each group were extirpated under ether anthesthesia. After cardiac tissues were formalin-fixed, paraffin-embedded sections were made, and hematoxylin-eosin (H&E) staining was conducted. Pathological investigations were conducted on stained heart tissue sections under the light microscope.

Figure 2:
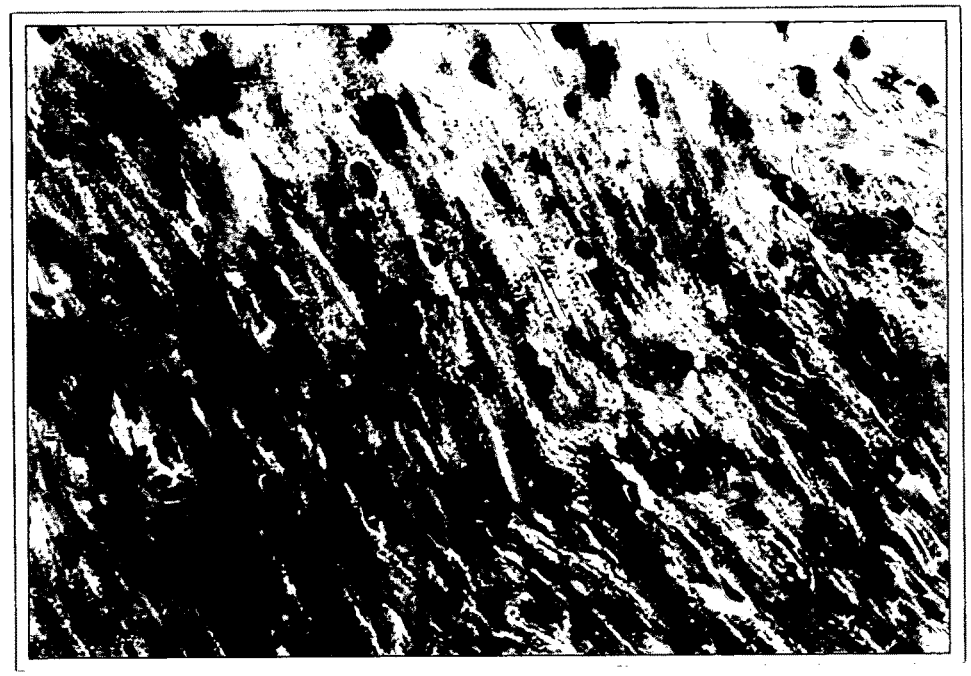
FIG. 2 is an optical microscopic photo (H&E stain, X400) of the left ventricular myocardial tissue of the batroxobin group.

In the left ventricular myocardial tissue of the batroxobin group (FIG. 2), abnormalities were not observed comparing to the left ventricular myocardial tissue of the control group.

Figure 3:
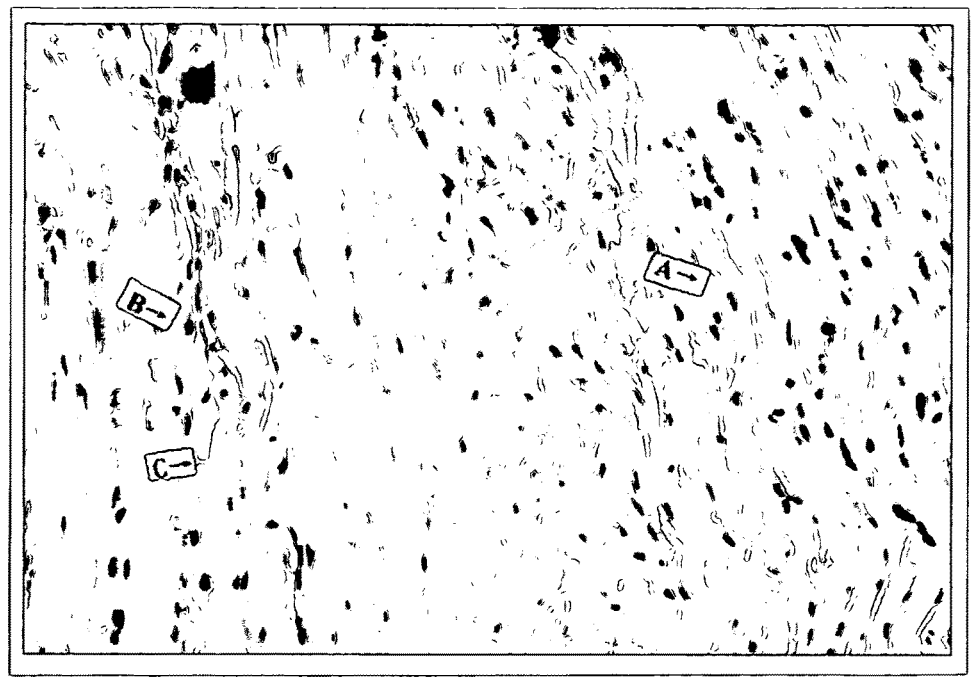
FIG. 3 is an optical microscopic photo (H&E stain, X200) of the left ventricular myocardial tissue of the adriamycin group.

On the other hand, in left ventricular myocardial tissue of the adriamycin group (FIG. 3), abnormalities were observed compared to the control group. Specifically the arrangement of the myocardial cells is disordered, and the pathological tissue called contraction bands (Arrow A), were observed. In the contraction band, some myocardial cells strongly contracted resulting agglutination to become a wave-like arrangement and the conventional striation structure of myocardial fiber has disappeared, and instead the acidophilic thick belt with a structure of no rule interval of myocardial cells was formed. Furthermore, myoplasm lysis or loss occurred in many myocardial cells, and cytoplasm staining became thin. Furthermore, in the myocardial cell, cell edema or acidophilic degeneration and necrosis (Arrow B) occurred, the intercellular space widens, and the edema (Arrow C) arose in the myocardial cell stroma. Such abnormalities cause myocardiopathies which lead to congestive heart failure and thus serves as an indication index of cardiotoxicity.

Figure 4:
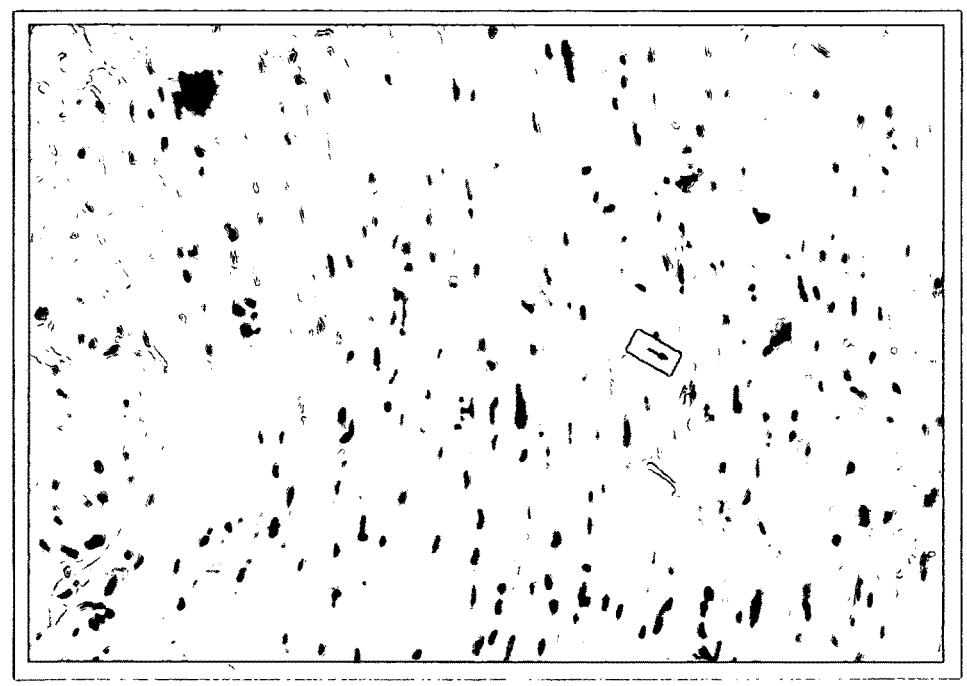
FIG. 4 is an optical microscopic photo (H&E stain, X200) of the left ventricular myocardial tissue of the batroxobin+ adriamycin group.

In contrast, the left ventricular myocardial tissue (FIG. 4) of the adriamycin+batroxobin group did not have the myocardial interstitial edema or contraction band formation that was seen in the adriamycin group. Moreover, although the dissolution of cytoplasm (Arrow) was obtained from a small number of myocardial cells, acidophilic degeneration was seldom seen.

It was confirmed in the present Example that degree of abnormality in the myocardial tissues of the adriamycin+batroxobin group was less than in the adriamycin group. Therefore it is understood that batroxobin can reduce the cardiotoxocity caused by adriamycin.

INDUSTRIAL APPLICABILITY

The present invention can reduce a side effect of an anticancer drug remarkably. Therefore, the present invention can be used in the cancer therapy by using the anticancer drug.

The invention claimed is:

1. A method of reducing a side effect due to the administration of adriamycin in a subject in need thereof, comprising administering 20 BU/kg of a thrombin-like enzyme to the subject once a day only after and not concurrently with the administration of adriamycin, wherein said side effect is cardiotoxicity.

2. The method according to claim 1, wherein the thrombin-like enzyme is a protease which generates fibrin I from fibrinogen.

3. The method according to claim 1, wherein the thrombin-like enzyme is selected from the group consisting of batroxobin, ancrod and crotalase.

4. The method according to claim 1, wherein the thrombin-like enzyme is batroxobin.

* * * * *